(12) United States Patent
Benhalima et al.

(10) Patent No.: US 7,292,895 B2
(45) Date of Patent: Nov. 6, 2007

(54) READY-TO-INSTALL ELECTRODE SYSTEM FOR CARDIOVERSION AND ASSEMBLY OF SAID SYSTEM AND AN ENDOSCOPE

(76) Inventors: Bouziane Benhalima, 43, Avenue Anatole, 93250 Villemomble (FR); Zohra Benhalima, 43, Avenue Anatole, 93250 Villemomble (FR)

( * ) Notice: Subject to any disclaimer, the term of this patent is extended or adjusted under 35 U.S.C. 154(b) by 0 days.

(21) Appl. No.: 10/554,753

(22) PCT Filed: Nov. 26, 2003

(86) PCT No.: PCT/FR03/03495

§ 371 (c)(1),
(2), (4) Date: Apr. 14, 2006

(87) PCT Pub. No.: WO2004/050174

PCT Pub. Date: Jun. 17, 2004

(65) Prior Publication Data

US 2006/0287680 A1    Dec. 21, 2006

(30) Foreign Application Priority Data

Nov. 27, 2002  (FR)  .................... 02 14842

(51) Int. Cl.
*A61N 1/00* (2006.01)
*A61B 1/00* (2006.01)
*A61B 5/04* (2006.01)

(52) U.S. Cl. ............ 607/124; 600/101; 600/104; 600/119; 600/121; 600/380; 600/373; 607/5; 607/116; 607/119; 607/152

(58) Field of Classification Search ................ 600/101, 600/104, 119, 121, 380, 373, 393, 439, 459; 607/2, 4, 5, 40, 115–7, 119, 124, 152
See application file for complete search history.

(56) References Cited

U.S. PATENT DOCUMENTS

| 4,149,538 | A | 4/1979 | McVay et al. | |
|---|---|---|---|---|
| 5,178,149 | A | 1/1993 | Imburgia et al. | |
| 6,099,464 | A * | 8/2000 | Shimizu et al. | 600/104 |
| 6,142,941 | A * | 11/2000 | Benhalima et al. | 600/439 |

(Continued)

FOREIGN PATENT DOCUMENTS

EP    0 104 287    4/1984

(Continued)

*Primary Examiner*—Kennedy J. Schaetzle
*Assistant Examiner*—Natasha Patel
(74) *Attorney, Agent, or Firm*—Young & Thompson

(57) ABSTRACT

A ready-to-install electrode system designed for use with an endoscope for performing cardioversion through the esophagus, and an assembly of the system and an endoscope. The system is characterized in that it includes a globally tubular protective cover (3) designed to be fitted on the endoscope (40) to cover at least the distal end of the endoscope, at least one electrode (2a-d) including a conductive electric membrane (21) connected to an electric conduction wire designed to be connected by its free end to a cardioversion apparatus, first and second fixing elements adapted to fix the at least one electrode respectively on the distal end of the endoscope and on the tubular wall (31) of the cover, such that the conductive membrane is directly accessible from outside the cover.

19 Claims, 3 Drawing Sheets

U.S. PATENT DOCUMENTS

| | | | |
|---|---|---|---|
| 6,394,949 B1 * | 5/2002 | Crowley et al. | 600/127 |
| 6,626,841 B1 * | 9/2003 | Atlee, III | 600/528 |
| 6,773,402 B2 * | 8/2004 | Govari et al. | 600/459 |
| 2005/0015132 A1 * | 1/2005 | Kronzon | 607/124 |

FOREIGN PATENT DOCUMENTS

| | | |
|---|---|---|
| WO | 90/13259 | 11/1990 |
| WO | 98/18519 | 5/1998 |

* cited by examiner

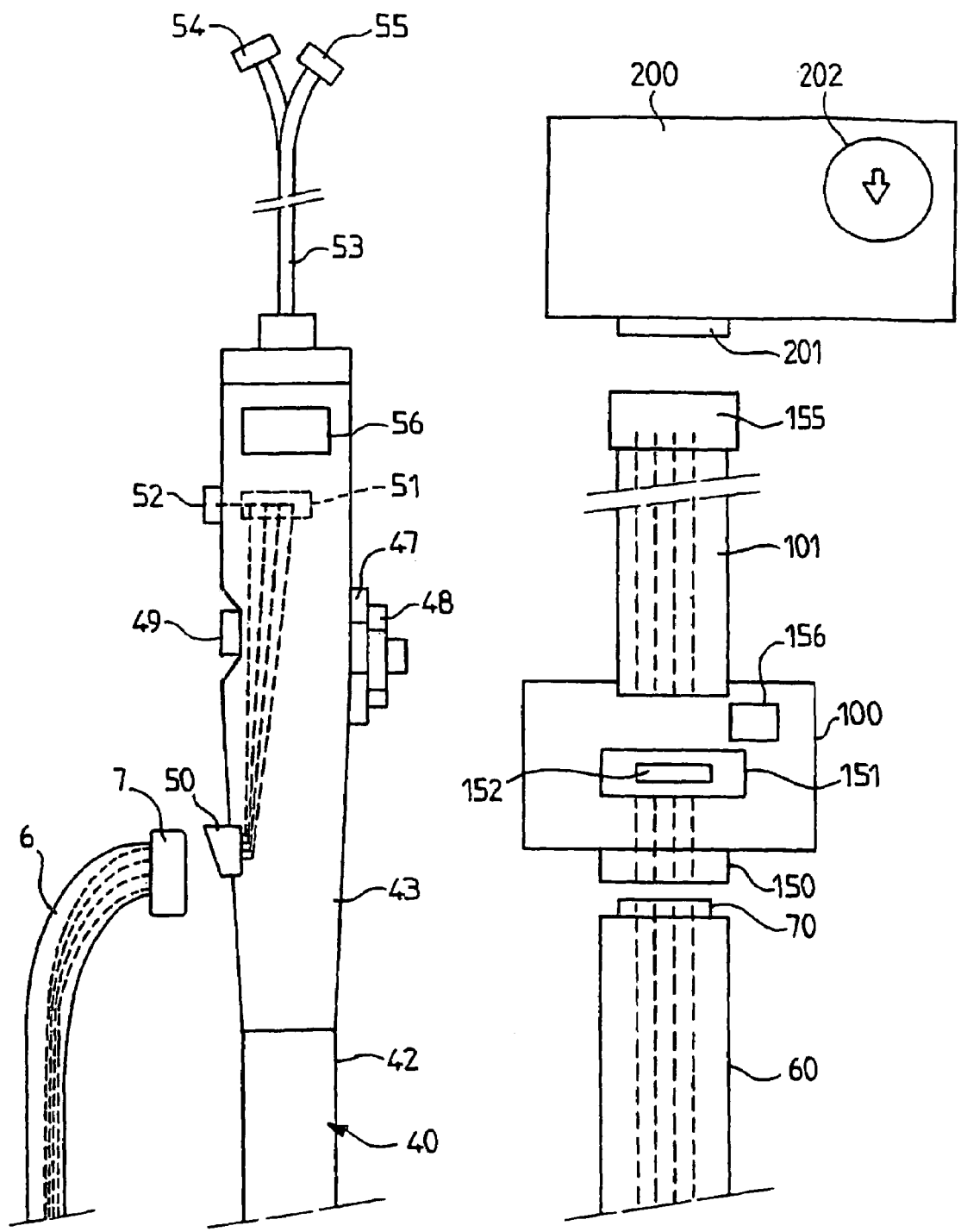

READY-TO-INSTALL ELECTRODE SYSTEM FOR CARDIOVERSION AND ASSEMBLY OF SAID SYSTEM AND AN ENDOSCOPE

FIELD OF THE INVENTION

This invention relates to a ready-to-install electrode system designed to be used with an endoscope for carrying out cardioversion esophageally, and an assembly of said system and an endoscope designed to be used to carry out cardioversion esophageally.

BACKGROUND OF THE INVENTION

To treat rhythm problems of a patient, and especially auricular fibrillation, it is known to initiate a procedure of cardioversion by electric shock. Such a cardioversion can lead to cerebral vascular events or to peripheral embolisms by detachment of part or all of a preexisting thrombus at the level of the left auricle. Thus, transesophageal echography is therefore generally performed prior to cardioversion in order to correctly visualize the left auricle and thus to detect the possible presence of a thrombus. A known probe for such a transesophageal echography generally comprises an ultrasonic sensor at the distal end of an endoscope.

One method of cardioversion in current use consists in producing electric shocks internally or by endocavitary means. Such a method constitutes an invasive procedure that is very difficult to implement. Another method consists in producing electric shocks externally by applying two electrodes to the patient's chest. This method is relatively easy to implement but requires general anesthesia.

Another method of cardioversion consists in producing electric shocks esophageally using an endoscope provided with several electrodes on its distal portion. This procedure requires simple sedation, but can produce complications when it follows prior transesophageal echography. Actually, in practice, the technician sometimes experiences problems in reinserting a new probe into the mouth of the patient where it can roll up because there is a risk of rejection of the probe by the patient due to the fact that the esophageal tissues are already irritated, to say nothing of the risks of lesion or perforation of the esophagus due to repeated insertions of endoscopes. To prevent such complications, the applicant suggested, in Application WO 98/18519, an endoscope equipped with an ultrasonic sensor and at least one electrode on its distal end that makes it possible to carry out both echography and transesophageal cardioversion during the same procedure, either simultaneously or in succession without the necessity of repeated insertion and removal of the probes through the esophagus. By using one electrode on the articulated portion of the endoscope near the ultrasonic sensor, such an endoscope, moreover, allows the technician to exactly visualize the location at which he wants to perform the cardioversion and to ensure close approach of the electrode to the wall of the heart, thus leading to especially effective cardioversion.

Moreover, for reasons of hygiene and public health safety, it is preferable to protect the distal ends of the endoscopes that are inserted into the esophagus for each procedure by means of a disposable latex or polyurethane protective cover. The use of such a protective cover proves incompatible with the presence of electrodes integrated on the distal end of an endoscope, because the electrical power released locally by the electrodes can melt or burn the thin wall of the cover. One possible solution that could be envisioned would consist in providing a cover that is made of a material with sufficient thermal resistance and thickness to resist the electrical power released by the electrodes. This solution, however, would entail a prohibitive cost, given the one-time use of the protective cover.

Consequently, in order to proceed under more certain conditions of hygiene and safety, physicians currently prefer to use cardioversion with electric shocks externally, in spite of its disadvantages.

OBJECT OF THE INVENTION

The purpose of this invention is to propose an electrode system that makes it possible to carry out cardioversion by endoscope that is easy to implement, effective in the treatment of rhythm difficulties, well tolerated by the patient and that is more certain in terms of hygiene and public health safety.

SUMMARY OF THE INVENTION

For this purpose, the object of this invention is a ready-to-install electrode system designed to be used with an endoscope for performing cardioversion esophageally, characterized by the fact that it comprises a protective cover of general tubular shape with a closed distal end and an open proximal end, said cover being designed to be fitted onto the endoscope to cover at least the distal end of the endoscope, at least one electrode comprising a conductive electrical membrane connected to an electrical conductive wire designed to be connected by its free end to a cardioversion apparatus, first fastening means that are able to make it possible for said at least one electrode to be fastened to the distal end of the endoscope, and the second fastening means that are able to make it possible for said at least one electrode to be fastened to the tubular wall of the cover in such a way that said conductive membrane is directly accessible from the outside of the cover.

According to one embodiment, the system according to the invention comprises at least one support strip that can be fastened by a first face, i.e., the inside face, to the endoscope by said first fastening means and that carries on its second face, i.e., the outside face, said at least one electrode, the tubular wall of said protective cover being provided with at least one opening with dimensions that are smaller than those of the support strip, the second fastening means being provided on the protective cover and/or the support strip to allow the support strip to be fastened by its second outside face against the inside face of the tubular wall of the protective cover, such that said at least one opening is closed and the conductive membrane of said electrode is accessible from the outside through said opening.

According to another embodiment, the electrode or electrodes are an integral part with the protective cover, for example by molding electrodes into the wall of the cover, the second fastening means being composed of the body itself of the cover, and the conductive wire(s) being able to be incorporated into the wall of the cover or be located along the inside face of the tubular wall of the cover.

According to one feature, the width of the opening of the protective cover is at least equal to the transverse dimension of the conductive membrane of the electrode such that said conductive membrane is accommodated through said opening when the support strip is fastened to the protective cover by the second fastening means.

According to another feature, the surface of the first inside face of the support strip comprises a first self-adhesive layer that comprises said first fastening means.

According to another feature, the second fastening means are composed of a second self-adhesive layer located on the periphery of the opening on the inside, face of the tubular wall of the protective cover and/or on the periphery of the second outside face of the support strip.

Advantageously, each self-adhesive layer is covered by a peelable film designed to be removed before the support strip is fastened.

The system according to the invention can advantageously comprise from 3 to 6 electrodes spaced lengthwise on the support strip, the tubular wall of the protective cover being provided with a longitudinal opening of corresponding length.

In one embodiment, the conductive wire or wires are carried by the support strip, extend up to the proximal transverse edge of the support strip and are accommodated starting from this proximal transverse edge in an insulating sheath connected on its opposite end to a connector that allows connection of the conductive wire or wires to the cardioversion apparatus.

Advantageously, the electrode or electrodes are covered by at least one protective film that can be removed before use of the electrode or electrodes.

The system according to the invention comprising the electrode or electrodes and the protective cover allows one-time use. The use of such a cover with electrodes according to the invention makes it possible to suggest a disposable cover at low cost relative to a possible approach that would consist in providing a cover that covers an endoscope equipped with electrodes, made of a material that can resist the electrical power released by the electrodes. Moreover, the covering of the electrodes integrated on the end of an endoscope by a latex or polyurethane cover makes cardioversion ineffective due to the nonconductive nature of such a cover. Thus, one possible approach that could have been envisioned would consist in furnishing a cover provided with conductive zones that are intended to face the electrodes. The cover according to the invention likewise costs clearly less than such a cover with conductive zones.

According to another feature, the system according to the invention comprises, moreover, an external control means composed of a box equipped with mounting means for allowing the mounting of said box on the proximal end of the endoscope, a first external connecting means such as an external receiving plug, to connect the conductive wire or wires of the electrode or electrodes, in particular, the connector of the above-defined sheath to the box, a second connecting means for connecting the box to the cardioversion apparatus, and a module for the electrical power charge designed to produce electric shocks and for triggering these shocks, said module being controlled by an external control element such as a button, and being connected to the first and the second connecting means.

The object of this invention is equally an assembly of the system as defined above and an endoscope equipped on its proximal end with a control handle designed to be used to carry out cardioversion esophageally, said assembly being characterized by the fact that the protective cover is fitted on the endoscope and covers at least the distal end of the endoscope, said at least one electrode is fastened, on the one hand, to the distal end of the endoscope by the first fastening means, and, on the other hand, to the tubular wall of the cover by the second fastening means such that said conductive membrane is directly accessible from the outside of the cover, said conductive wire being connected by its free end to a first external connecting means located at the level of said control handle.

In a first variant, the control handle integrates an internal cardioversion control means, said system comprising a module for the electrical power charge that is intended to produce the electrical shocks and for triggering these shocks, said module being controlled by an external control element and being connected to said first connecting means, such as an external receiver plug, for connecting the conductive wire or wires of the electrode or electrodes, especially the connector of the above-defined sheath, and to a second connecting means for connecting it to the cardioversion apparatus.

In a second variant, the assembly comprises an external control means comprising a box equipped with mounting means for allowing the installation of said box on the proximal end of the endoscope, said first external connecting means, such as an external receiving plug, for connecting the conductive wire or wires of the electrode or electrodes to the box, a second connecting means for connecting the box to the cardioversion apparatus, and a module for the electric power charge designed to produce electric shocks and for triggering these shocks, said module being controlled by an external control element and being connected to the first and the second connecting means.

Advantageously, a distal portion of the endoscope is equipped with an ultrasonic sensor in such a way as to form a device that allows both echography and esophageal cardioversion to be carried out. Advantageously, the distal portion of the endoscope that comprises the sensor is articulated relative to the remainder of the endoscope, at least one electrode being fastened on both sides of the articulation.

The assembly according to the invention can be mounted by carrying out the following steps: fastening the support strip by its first inside face on the distal end of the endoscope, fastening the support strip by its second outside face on the internal wall of the protective cover, such that the electrode or electrodes are located at the level of one opening of said protective cover, and connection of the electrode or electrodes to a cardioversion control means connected to a cardioversion apparatus. Advantageously, the stage of fastening the support strip to the distal end of the endoscope is carried out before the stage of fastening the support strip to the protective cover.

BRIEF DESCRIPTION OF THE DRAWINGS

The invention will be better understood and other objectives, details, characteristics and advantages will become more clear in the course of the following detailed explanatory description of two particular currently preferred embodiments of the invention, given solely for purposes of illustration and in no way to be construed as limiting, with reference to the attached schematic drawings.

In this drawing:

FIG. 5 is a partial schematic view of a cardioversion control handle according to a first variant; and FIG. 6 is a schematic and plan view of a cardioversion control system according to a second variant.

DETAILED DESCRIPTION OF THE INVENTION

Figure 1:
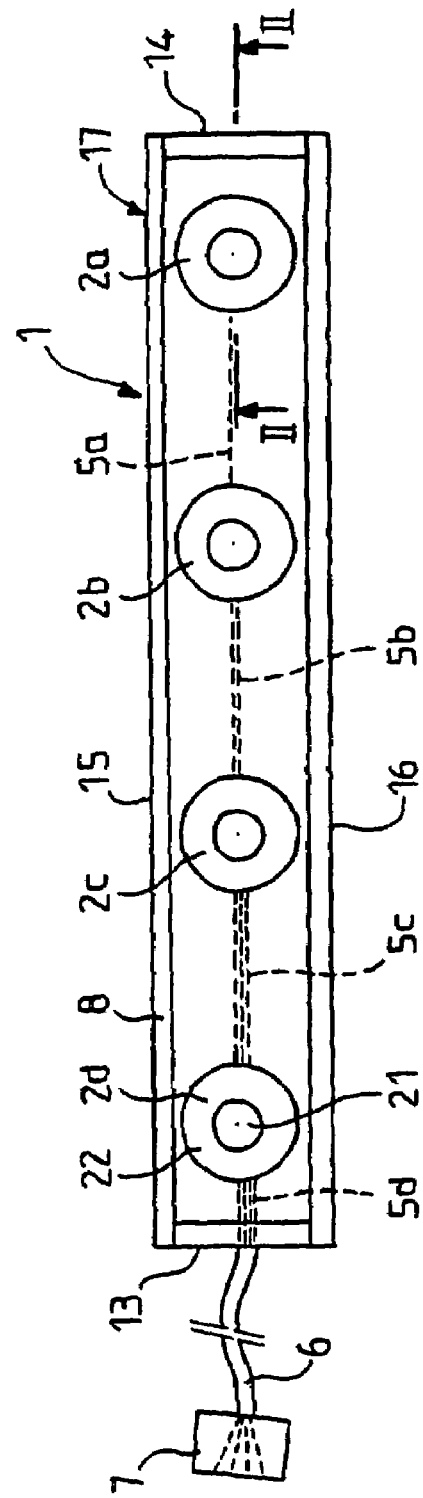
FIG. 1 shows a top view of a support strip bearing electrodes of a ready-to install electrode system according to the invention.

According to the embodiment shown in the figures, the electrode system according to the invention comprises a support strip 1 bearing the electrodes 2a-d and a separate protective cover 3.

The support strip 1 of rectangular shape has a first face 11, called the inside face, with a completely adhesive surface. This inside face 11 is completely covered by a peelable film 4 designed to be removed before application of the support strip to the distal end of an endoscope, as described below. The support strip is made of a nonconductive flexible material. As a variant, there could be provided an inside face whose surface has one or more adhesive layers allowing good fastening of the support strip to the endoscope to be ensured. Four identical electrodes 2a-d are located longitudinally on the second face 12 of the strip, called the outside face, opposite the lower face 11. In the known manner, each electrode comprises a circular conductive membrane 21 supported by a nonconductive protective membrane 22, for example of circular shape, by which the electrode is fastened by bonding to the outside face 12 of the support strip, the conductive membrane being essentially located parallel to the support strip 1. The protective membrane 21 covers the circular periphery of the conductive membrane so as to protect the esophagus against local burns due to electrical discharges during cardioversion, in particular when using a high power level. The conductive membranes 21 of the electrodes are each connected to a conductive wire 5a-d. Each conductive wire 5a-d is soldered by one end to the conductive membrane 21 of one electrode, extends perpendicular to the conductive membrane from this soldered end through the protective membrane 22, crosses the support strip 1 and extends lengthwise along the lower face 11, in the direction of one of the transverse edges of the strip, called the proximal edge 13. The conductive wires, spaced crosswise from one another, stick to the adhesive surface of the lower face 12 of the support strip and are sandwiched between said lower face and the peelable film 4. At the level of the proximal edge 13, the conductive wires are located in an insulating sheath 6. The insulating sheath is fastened by one end to the proximal edge 13 and ends on its other end by a connector 7 to allow electrical connection of the four conductive wires to the cardioversion control means described below.

In a variant embodiment, it could be provided that the conductive wires be located on the outside face of the support strip, the conductive wires then being kept spaced apart from one another against the outside face by adhesive strips located between the electrodes, or that they be located between the two layers of a composite support strip.

The outside face 12 of the support strip has a surface comprising a peripheral adhesive layer 17 that is composed of two longitudinal portions and two transverse portions, formed respectively along the longitudinal edges 15, 16 and transverse edges 13, 14 of the support strip. This adhesive layer 17 is covered by a peelable film 8 composed of four portions, two of them covering the adhesive layer 17 along the longitudinal edges, the other two covering the adhesive layer along the proximal edge 13 and the distal edge 14.

Figure 2:
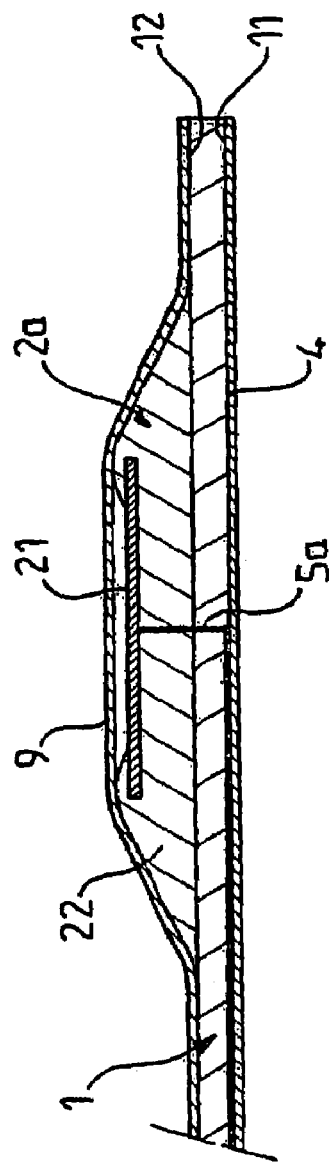
FIG. 2 shows a partial, enlarged very schematic cross-sectional view of the support strip of FIG. 1, along plane II-II.

The electrodes are completely covered by a protective film 9, shown only in FIG. 2, for reasons of clarity, intended to be removed before use of the electrodes. This protective film 9 and the peelable film 8 are located edge-to-edge. In a variant embodiment, the protective film 9 just covers said peelable film, the removal of the protective film thus allowing the peelable film to be likewise removed. In another variant embodiment, the protective film likewise comprises the peelable film that covers the adhesive layer 17. Covering each electrode with an individual protective film could likewise be provided.

Figure 3:
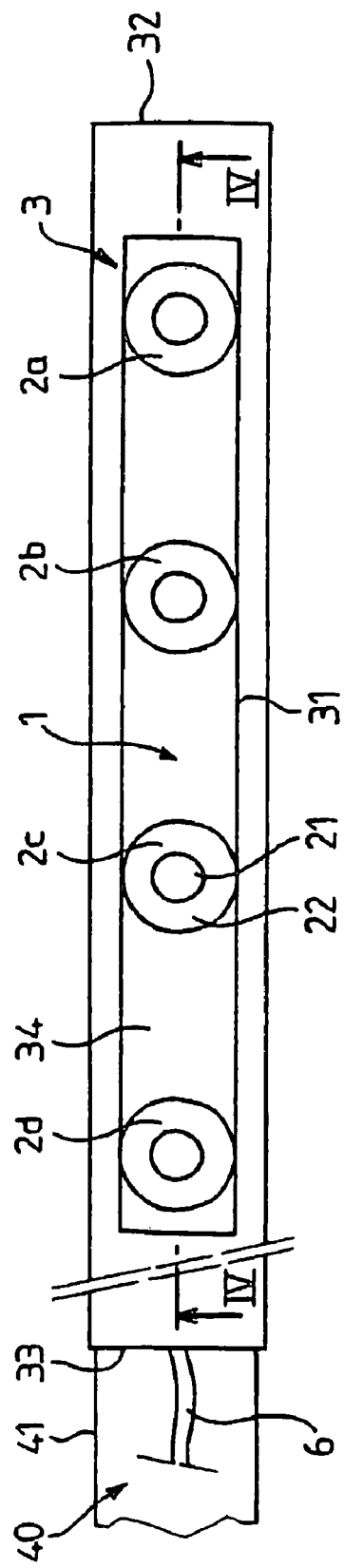
FIG. 3 is a partial external view of the assembly according to the invention.
Figure 4:
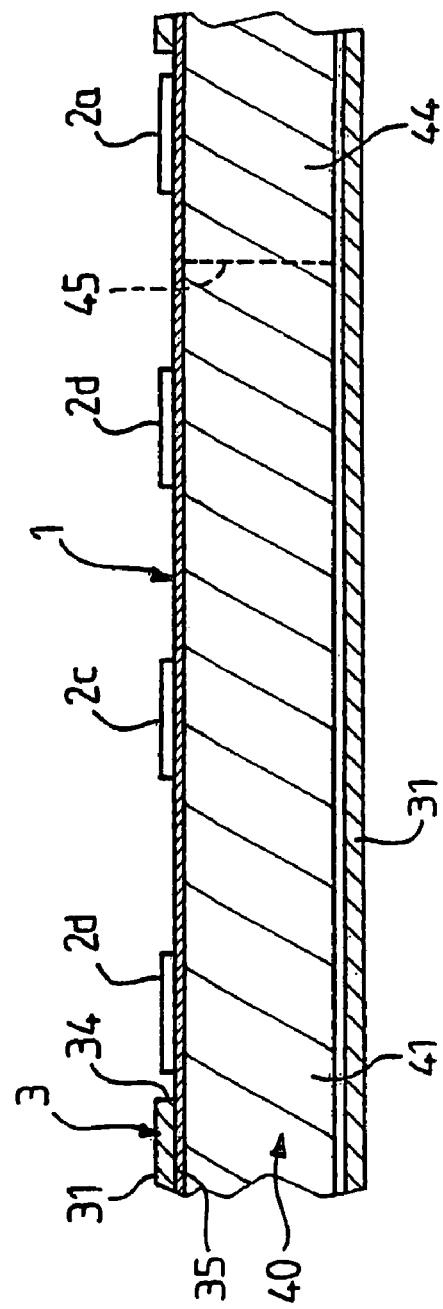
FIG. 4 is a partial cutaway view of FIG. 3 along plane IV-IV.

With reference to FIGS. 3 and 4, the protective cover 3 is formed by a tubular wall 31 made of insulating flexible plastic material, for example latex or polyurethane, with a closed distal end 32, and an open proximal end 33 by which the cover can be slipped on over the distal end of an endoscope. The length of the cover is designed to cover the entire portion of the endoscope that will be inserted by way of the mouth of the patient. According to the invention, the tubular wall 31 of the cover comprises a rectangular longitudinal opening 34 that crosses the tubular wall from one side to the other. The length of the opening is less than the length of the strip and is at least equal to the length of the support strip on which the electrodes are arranged, and preferably less than or essentially equal to the length separating the two crosswise portions of the adhesive layer 17. The width of the opening is for its part less than the width of the support strip and is essentially greater than or equal to the diameter of the conductive membranes of the electrodes. To ensure optimum contact between the electrodes and the auricular tissue at the instant of cardioversion, the width of the opening 34 is preferably less than or approximately equal to the length separating the two longitudinal portions of the adhesive layer 17 and essentially greater than or equal to the diameter of the nonconductive protective membranes 22 of the electrodes. By way of example, the width of the opening is essentially equal to the diameter of the protective membranes 22, as is shown in FIG. 3.

The support strip and the cover are designed to be positioned on the distal end 41 of the flexible tubular endoscope 40, with a known structure, connected on its proximal end 42 to a control handle 43 as is shown in FIG. 4. Advantageously, the support strip and the cover can be used with an endoscope comprising on its distal end 41 a multiplane ultrasonic sensor to allow both echography and cardioversion. The multiplane sensor (not shown) is positioned on a distal portion 44 that is articulated with respect to the remainder of the endoscope. This articulation is shown schematically by reference number 45 in FIG. 4. In the known manner, the articulated portion 44 can be mechanically maneuvered flexurally via a control guide (not shown) that is accommodated coaxially in the endoscopic tube by two rollers 47, 48 provided on the handle, each equipped with a brake. The handle is provided with another manual roller 49 that allows rotary control of the cutting plane of the ultrasonic sensor that is mechanically directed annularly.

The support strip and the protective cover can be used in the following manner. The peelable film 4 is removed from the inside face of the adhesive surface and the support strip is fastened by this face to the distal end 41 of the endoscope, such that the electrode 2a, the nearest to the distal edge 14 of the support strip, is fastened to the articulated distal portion 44 of the endoscope, between the sensor and the articulation 45, and the other three electrodes 2b, 2c, and 2d are positioned on the unarticulated portion 44 of the distal end 41 of the endoscope in the vicinity of the articulation. The conductive wires are then located between the tubular wall of the endoscope and the support strip. The cover is then fitted onto the distal end of the endoscope. The four portions of the peelable film 8 and the protective film 9 are removed, and the cover is fastened to the support strip by bonding by means of the adhesive layer against the inside face 35 of the tubular wall of the cover, around the opening 34, by manually applying pressure to the outside face of the tubular wall of the cover. FIGS. 4 and 5 illustrate the system according to the invention after fastening to the distal end of the endoscope. Alternatively, the cover and the support strip can be combined with one another after having removed the peelable film 8 and the protective film 9; this assembly is then fitted over the distal end of the endoscope and the strip is bonded to the endoscope. In this case, the peelable film 4 can be removed before or after positioning of said combination on the endoscope. To facilitate this operation of removal of the peelable film 4, a peelable film equipped with a tongue can be provided, starting from the distal edge 14 of the support strip and extending over a length such that its free end is accessible from the outside when the support strip is fastened to the protective cover.

By way of example, although not shown in the figures, the strip measures from 15 to 20 centimeters and the four electrodes are arranged over a length of roughly 12 to 15 centimeters. Each electrode has a diameter from roughly 1.5 to 2 centimeters. The distance between the outermost distal electrode 2a and the following electrode 2b is from roughly 2 to 2.5 centimeters, whereas the remaining electrodes are spaced from 1 to 2 centimeters only. The strip is fastened to the endoscope such that the outermost distal electrode is placed at a distance of roughly 3.5 to 4.5 centimeters from the distal tip of the endoscope in its articulated portion 44.

The electrodes can thus be positioned exactly at the desired location on the endoscope. Moreover, the cover is fastened to the endoscope via the support strip; this ensures that the cover is securely kept on the endoscope and facilitates handling of the assembly, in particular when the endoscope is being withdrawn from the esophagus. It is desirable that the bonding of the support strip to the cover ensures a seal at least relative to the liquids and juices present in the esophagus. Such a sealed bonding of the support strip to the cover makes it possible to avoid any contamination of the endoscope while it is being used and thus to simplify the process of washing the latter between two procedures. To ensure proper bonding of the cover to the support strip bearing the electrodes, the support strip can comprise a marker, such as a transverse line of red color, located on the outside face 12 of the support strip between the outermost distal electrode 2a that is designed to be fastened to the articulated distal portion of an endoscope and the following electrode 2b that is designed to be fastened to the unarticulated portion 44 of the distal end of the endoscope. The distance that separates this marker line of the outermost distal electrode 2a will be defined as a function of the different types of endoscope that is available commercially. In this way, the technician begins by fastening the support strip at the level of the articulation line 45 of the endoscope using this marker and then fastens the remainder of the support strip. Thus, the cover will be perfectly bonded onto the support strip, and the seal will be maintained. In a variant embodiment, an adhesive layer could be provided on the inside face 35 of the tubular wall of the cover, surrounding the opening and covered by a peelable film to replace or supplement the adhesive layer 17 provided on the outside face of the support strip.

When cardioversion has been completed, the cover and the support strip can be removed from the distal end of the endoscope. Adhesion of the support strip to the endoscope and adhesion of the support strip to the cover can be determined such that when the technician removes the cover, the support strip remains fastened to the endoscope, or such that the support strip remains fastened to the protective film during removal of the cover by the technician. This latter approach is preferred because it allows maximum limitation of the risks of endoscope contamination.

In the case of use of a cover for an endoscope for echography equipped with an ultrasonic sensor, a gel designed to cover the ultrasonic sensor to obtain correct visualization through the cover during echography can be placed on the closed distal end 32. A rigid clip closure system (not shown) is arranged on the distal end of the endoscope and will catch the wall of the cover between the distal end 32 and the opening 34, for example 2-3 centimeters from the distal end to keep the gel in the cover. After having manually removed the closure system, the distal end of the endoscope is inserted into the cover, and the ultrasonic sensor is covered automatically by the gel. The presence of this gel in situ makes it possible to avoid the stage of adding the gel by the physician, by means of a syringe inserted through the open proximal opening of the cover.

The sheath 6 of suitable length is located along the endoscope and can be assembled with the latter by any appropriate means. In a first variant shown in FIG. 5, the system according to the invention comprises a cardioversion control means that is integrated on the control handle 42 of the endoscope and to which the connector 7 of the sheath 6 is connected. The control handle comprises a receiving plug 50 to allow connection of the connector to a module 51 that is integrated into the handle. Since this module is used to charge selected power and to perform cardioversion, it is controlled by an external control button 52. A cable 53 makes it possible to connect the handle, on the one hand, to an echography apparatus and, on the other hand, to a cardioversion apparatus. The end of the cable 53 forks into two connectors, a first connector 54 that makes it possible to connect the ultrasonic sensor to an echography apparatus, and a second connector 55 that makes it possible to connect the module 51 to a cardioversion apparatus. The control handle 52, moreover, comprises a digital display screen 56 for indicating the number of Joules of electric charge to be triggered, as well as an indicator light equipped with an audio warning system to indicate the end of the power charging.

In another variant embodiment shown in FIG. 6, the cardioversion control means is formed by a box 100 that is independent of the handle, but able to be assembled on the latter. The box 100 comprises a control module 151 controlled by a button 152 and interposed between a receiving plug 150 allowing connection to the module 151 of the connector 70 of a sheath 60 containing the electrode conductive wires and an output cable 101 provided on its end with a connector 155 that allows connection to a cardioversion apparatus 200 via an additional receiving plug 201. In the known manner, the cardioversion apparatus comprises a capacitor that can deliver the selected charge manually by an external switch 202. The box 100 comprises assembly means (not shown) that allow the box to be assembled on the handle of an endoscope. The box comprises, moreover, a digital display screen 156 to indicate the number of Joules of the electrical charge to be triggered, which was selected by the switch 202 of the cardioversion apparatus, as well as an indicator light equipped with an audio warning system to indicate the end of power charging.

The two above-described control means are used as follows. After having selected the appropriate electrical power charge, the technician, by briefly pressing on the control button, controls the charging of the capacitor of the cardioversion apparatus under the control of the screen light equipped with an audio warning system to indicate the end of the selected charge. Once charging has been completed, pressing again on the same button allows triggering of the discharge by the electrodes for restoring the sino-auricular rhythm. With this integrated control means on the handle or assembled with the handle, the technician can manage the cardioversion procedure without a third person. The independent control means described above makes it possible to adapt the electrode system according to the invention to any type of endoscope that exists on the market.

Although the invention has been described in conjunction with two particular embodiments, it is quite apparent that it is in no way limited thereto and that it comprises all the technical equivalents of the described means as well as their combinations if they fall within the framework of the invention. Since the system according to the invention comprises the support strip and protective cover, it can be used with any type of endoscope, whether intended for echography or not. As described above, the electrodes can be placed on the articulated distal portion of an endoscope, whether the latter is articulated manually or by using a shape memory material, for example. Of course, it will be possible to adapt the length of the opening as a function of the number of electrodes carried by the support strip that can vary, preferably from 3 to 6, and the dimensions of the opening of the cover can, of course, be adapted to the number and type of electrodes.

The invention claimed is:

1. Ready-to-install electrode system designed to be used with an endoscope to carry out cardioversion esophageally, characterized by the fact that it comprises a protective cover (3) of general tubular shape with a closed distal end (32) and an open proximal end (33), said cover being designed to be fitted onto the endoscope (40) to cover at least the distal end (41) of the endoscope, at least one electrode (2*a-d*) comprising an electrically conductive membrane (21) connected to an electrically conductive wire (5*a-d*) designed to be connected by its free end to a cardioversion apparatus, first fastening means that allow said at least one electrode to be fastened to the distal end (41) of the endoscope, and second fastening means (17) that allow said at least one electrode to be fastened to the tubular wall (31) of the cover in such a way that said conductive membrane is directly accessible from the outside of the cover, which further comprises at least one support strip (1) that can be fastened by a first inside face (11), to the endoscope by said first fastening means, and that carries on a second outside face (12), said at least one electrode (2*a-d*), the tubular wall (31) of said protective cover (3) being provided with at least one opening (34) with dimensions less than those of the support strip, the second fastening means (17) being provided on the protective cover and/or the support strip to allow the support strip to be fastened by its second outside face (12) against the inside face (35) of the tubular wall of the protective cover, such that said at least one opening is closed and that the conductive membrane of said electrode is accessible from the outside through said opening.

2. System according to claim 1, wherein the width of the opening (34) of the protective cover is at least equal to the crosswise dimension of the conductive membrane (21) of the electrode (2*a-d*) such that said conductive membrane is accommodated through said opening when the support strip (1) is fastened to the protective cover by the second fastening means (17).

3. System according to claim 2, wherein the surface of the first inside face (11) of the support strip (1) comprises a first self-adhesive layer that constitutes said first fastening means.

4. System according to claim 2, wherein the second fastening means are composed of a second self-adhesive layer (17) located on the periphery of the opening (34) on the inside face (35) of the tubular wall (31) of the protective cover (3) and/or on the periphery (13-16) of the second outside face (12) of the support strip (1).

5. System according to claim 1, wherein the surface of the first inside face (11) of the support strip (1) comprises a first self-adhesive layer that constitutes said first fastening means.

6. System according to claim 5, wherein the second fastening means are composed of a second self-adhesive layer (17) located on the periphery of the opening (34) on the inside face (35) of the tubular wall (31) of the protective cover (3) and/or on the periphery (13-16) of the second outside face (12) of the support strip (1).

7. System according to claim 1, wherein the second fastening means are composed of a second self-adhesive layer (17) located on the periphery of the opening (34) on the inside face (35) of the tubular wall (31) of the protective cover (3) and/or on the periphery (13-16) of the second outside face (12) of the support strip (1).

8. System according to claim 7, wherein each self-adhesive layer is covered by a peelable film (4) designed to be removed before the support strip (1) is fastened.

9. System according to claim 1, wherein it comprises from 3 to 6 electrodes (2*a-d*) spaced lengthwise on the support strip (1), the tubular wall (31) of the protective cover being provided with a longitudinal opening (34) of corresponding length.

10. System according to claim 1, wherein the conductive wire or wires (5*a-d*) are borne by the support strip (1), extend up to the proximal transverse edge (13) of the support strip and are accommodated starting from this proximal transverse edge (13) in an insulating sheath (6) connected on its opposite end to a connector (6, 60) that allows connection of the conductive wire or wires to the cardioversion apparatus.

11. System according to claim 1, wherein the electrode or electrodes (2*a-d*) are covered by at least one protective film (9) that can be removed before use of the electrode or electrodes.

12. System according to claim 1, wherein it comprises, moreover, an external control means composed of a box (100) equipped with mounting means for allowing the mounting of said box on the proximal end of the endoscope, a first external connecting means (150), to connect the conductive wire or wires (5*a-d*) of the electrode or electrodes (2*a-d*), a second connecting means (101, 155) for connecting the box to the cardioversion apparatus (200), and a module (151) for the electric power charge designed to produce electric shocks and for triggering these shocks, said module being controlled by an external control element (152) and being connected to the first and the second connecting means.

13. Assembly of the system according to claim 1 and an endoscope (40) equipped on its proximal end (42) with a control handle (43) designed to be used to carry out cardioversion esophageally, wherein the protective cover (3) is fitted on the endoscope (40) and covers at least the distal end (41) of the endoscope, said at least one electrode (2*a-d*) is fastened, on the one hand, to the distal end (41) of the endoscope by the first fastening means, and, on the other hand, to the tubular wall of the cover by the second fastening means (17) such that said conductive membrane is directly accessible from the outside of the cover, said conductive wire (5a-d) being connected by its free end to an external connecting means (50, 150) located at the level of said control handle.

14. Assembly according to claim 13, wherein the control handle (43) integrates an internal cardioversion control means, said system comprising a module (51) for the electric power charge that is intended to produce the electrical shocks and for triggering these shocks, said module being controlled by an external control element (52) and being connected to said first external connecting means (50) for connecting the conductive wire or wires (5a-d) of the electrode or electrodes, and to a second connecting means (55) for connecting it to the cardioversion apparatus.

15. Assembly according to claim 14, wherein a distal portion (41) of the endoscope is equipped with an ultrasonic sensor in such as way as to form a device that allows both echography and esophageal cardioversion to be carried out.

16. Assembly according to claim 13, wherein it comprises an external control means comprising a box (100) equipped with mounting means for allowing the mounting of said box on the proximal end (42) of the endoscope, said first external connecting means (150) for connecting the conductive wire or wires (5a-d) of the electrode or electrodes (2a-d) to the box, a second connecting means (101, 155) for connecting the box to the cardioversion apparatus (200), and a module (151) for the electric power charge designed to produce electric shocks and for triggering these shocks, said module being controlled by an external control element (152) and being connected to the first and the second connecting means.

17. Assembly according to claim 16, wherein a distal portion (41) of the endoscope is equipped with an ultrasonic sensor in such as way as to form a device that allows both echography and esophageal cardioversion to be carried out.

18. Assembly according to claim 13, wherein a distal portion (41) of the endoscope is equipped with an ultrasonic sensor in such as way as to form a device that allows both echography and esophageal cardioversion to be carried out.

19. Assembly according to claim 18, wherein the distal portion (44) of the endoscope (40) that comprises the sensor is articulated relative to the remainder of the endoscope, at least one electrode (2a) being fastened on both sides of the articulation.

* * * * *